(12) United States Patent  
Bowden (10) Patent No.: US 7,862,703 B2
(45) Date of Patent: Jan. 4, 2011

(54) DIAGNOSTIC AND CONTROL METHODS FOR INTERNALLY CALIBRATED OXYGEN SENSOR

(75) Inventor: Mark Edward Bowden, Arlington, MA (US)

(73) Assignee: General Electric Company, Schenectady, NY (US)

( * ) Notice: Subject to any disclaimer, the term of this patent is extended or adjusted under 35 U.S.C. 154(b) by 514 days.

(21) Appl. No.: 12/041,190

(22) Filed: Mar. 3, 2008

(65) Prior Publication Data

US 2008/0149500 A1 Jun. 26, 2008

Related U.S. Application Data

(62) Division of application No. 10/774,491, filed on Feb. 10, 2004, now Pat. No. 7,338,592.

(51) Int. Cl.
G01N 27/41 (2006.01)

(52) U.S. Cl. .................. 205/784; 73/1.06; 204/425; 204/427

(58) Field of Classification Search .................. 204/400, 204/424, 425, 427; 205/784, 784.5; 73/1.06
See application file for complete search history.

(56) References Cited

U.S. PATENT DOCUMENTS 6,177,001 B1   1/2001   Meyer

FOREIGN PATENT DOCUMENTS

| EP | 53139965 | 11/1978 |
|---|---|---|
| EP | 0 810 433 | 12/1997 |
| JP | 52-71293 | 6/1977 |
| JP | 05209860 A | 8/1993 |
| JP | 02128155 A | 5/2000 |
| JP | 2000146904 A | 5/2000 |

OTHER PUBLICATIONS

International Search Report mailed Apr. 1, 2005.
David M. Haaland, "Internal-Reference Solid-Electrolyte Oxygen Sensor", Analytic Chemistry, vol. 49 No. 12, Oct. 1977, pp. 1813-1817.

(Continued)

Primary Examiner—Kaj K Olsen
(74) Attorney, Agent, or Firm—Nixon & Vanderhye P.C.

(57) ABSTRACT

A method for pumping a sealed internal reference chamber of a solid electrolyte oxygen sensor, having an internal electrode and an external electrode, during a dynamically controlled, null balancing, calibration process, the method including: initializing a set of pumping current pulse parameters controlling pulse ON time, post pulse relaxation time and pulse magnitude; applying a pulsed pumping current based on the set of pulse parameters to the internal and external electrodes, wherein the application of current transitions the chamber from a substantially evacuated state to a substantially null or balanced oxygen partial pressure state with respect to an applied external calibration gaseous environment; periodically comparing the Nernst voltage of the sensor to a predetermined limit to determine whether the chamber is at a null or balanced state; comparing an elapsed time from the application of the pulsed pumping current to a third predetermined time limit to determine if the sensor has failed, and progressively reducing at least one of the magnitude, ON time and relaxation time of the pumping current pulses to slow the transition as the chamber approaches the null or balanced oxygen partial pressure state.

22 Claims, 5 Drawing Sheets

OTHER PUBLICATIONS

William C. Maskell, "Progress in the Development of Zirconia Gas Sensors", Solid State Ionics 134 (2000), pp. 43-50.

H. Kaneko et al., "Miniature Oxygen Pump-Gauge, 1. Leakage Considerations", Received Apr. 11, 1986, pp. 161-172.

JP2006-552131, Japan Patent Office Search Report and Written Opinion, Jul. 21, 2010.

DIAGNOSTIC AND CONTROL METHODS FOR INTERNALLY CALIBRATED OXYGEN SENSOR

RELATED APPLICATION

This application is a divisional application of U.S. patent application Ser. No. 10/774,491 (U.S. Pat. No. 7,338,592) filed Feb. 10, 2004, the entirety of which is incorporated by reference.

BACKGROUND OF THE INVENTION

The present invention relates, in general, to the control of solid electrolyte sensors used to detect the level of oxygen in a gaseous environment and, in particular, to the control of oxygen sensors, containing a pump-able sealed internal reference chamber.

Figure 5:
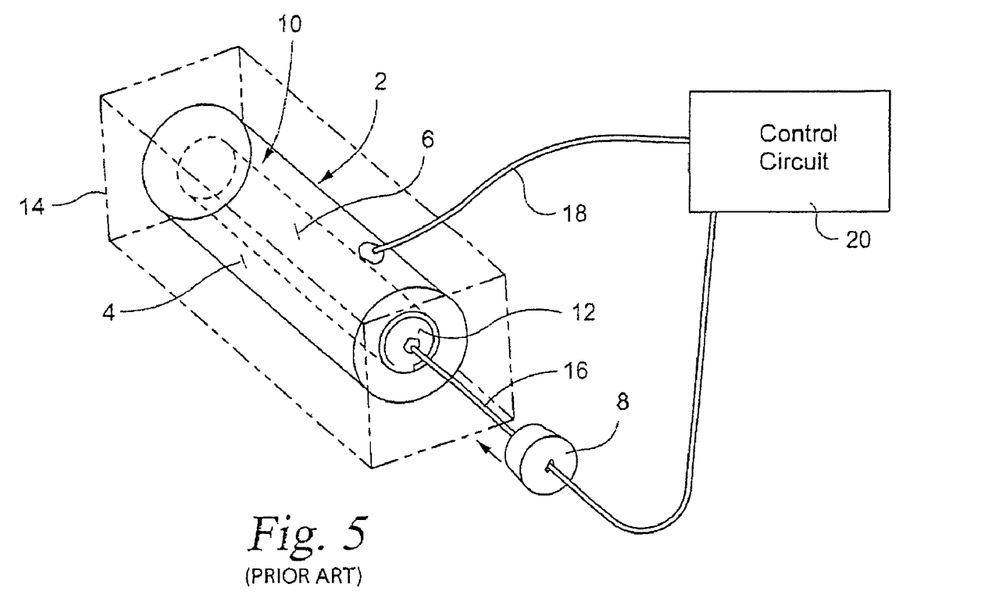
FIG. 5 is a schematic diagram showing a solid electrolyte oxygen cell.
Figure 6:
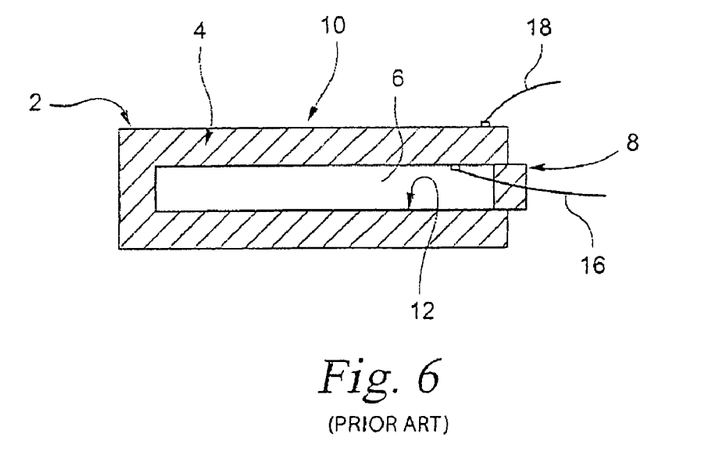
FIG. 6 is a schematic diagram showing in cross-section the oxygen cell.

A conventional solid electrolyte oxygen sensor is described in U.S. Pat. No. 6,177,001 ('001 patent). FIGS. 5 and 6 show a conventional sensor 2 formed of a solid oxide material, typically zirconia that includes a tubular shell 4 that is closed at one end. The shell forms a cylindrical chamber 6 that is sealed, for example, by having a plug 8 at the open end of the tube shell. The outside surface 10 of the oxide tubular shell is coated with porous platinum to create an outer electrode exposed to gases external to the sensor, such as in a heated environment 14. The cylindrical inside surface 12 of the oxide shell is coated with porous platinum to create an inner electrode exposed to the gas in the chamber 6. The inner and outer platinum electrodes and the solid oxide material separating them comprise a single cell oxygen sensor 2 that functions according to the Nernst principle when the cell is operated at an elevated temperature, typically greater than 700° C. The sensor 2 is typically mounted in an oven 14 or other high temperature environment.

A common mode of operation of the sensor 2 is to provide a reference gas of known oxygen partial pressure, typically air, to one of the two electrode surfaces, e.g., the inside surface 12 of the shell 4. A process gas with unknown oxygen partial pressure is provided to the second electrode surface, e.g., the outside surface 10 of the shell 4. The relationship of the voltage output of the sensor to an imbalance in the two oxygen partial pressures is defined by the Nernst equation:

$$E_{12} = \frac{RT}{4F} \times \ln\left(\frac{P1}{P2}\right)$$

Where: $E_{12}$ is the developed electromotive force; R is the universal gas constant; T is the absolute temperature; F is the Faraday constant; P1 is the process gas oxygen partial pressure, and P2 is the reference gas oxygen partial pressure. By proper manipulation of the Nernst equation the sensor can be made to give an indication of the oxygen partial pressure in an unknown gaseous environment.

The reference gas is contained within the chamber 6 defined by the inside surface 12 of the shell and the plug 8 that seals the gas into the shell. A lead wire 16 is passed through the plug and affixed to the inner electrode surface. A second lead wire 18 is affixed to the outer electrode surface 10. The inner and outer leads 16, 18 form electrical connections between the sensor 2 and a suitable control circuit 20.

When the sensor 2 is in a high temperature environment 14, oxygen ions can be made to flow though the temperature activated solid electrolyte in response to the application of a pumping current to the porous platinum electrodes of the inner and outer surfaces 12, 10 of the tubular shell 4. The polarity of the applied current determines the direction of the ionic oxygen flow with said flow being in opposition to the applied current polarity. In this manner the oxygen partial pressure in the sensor sealed internal reference chamber 6 can be substantially altered as a function of the current applied to the electrode surfaces 10, 12.

The pumping current may be applied in discrete amounts, or pulses, to remove oxygen from the sealed reference chamber until the chamber is determined to be effectively empty as indicated by the Nernst voltage reaching a predetermined value. In a further step, the pumping current polarity is reversed and pulses are applied to the electrodes 10, 11 to cause oxygen to flow from a prevailing external gaseous environment, typically a gas with known oxygen partial pressure such as air, into the previously emptied sealed internal reference chamber. In particular, the application of pumping current is in a pulsed mode comprising in the first instance, a pulse with controlled height and width and in the second instance, a measurement interval during which no pumping current is applied to the sensor but during which a sensor voltage reading is taken to determine the level of oxygen in the sealed internal chamber 6 in relation to the level of oxygen in the prevailing external environment. The application of this two-step, pump-measure process continues until the measured output voltage reaches a predetermined value, typically zero volts or null. At this null state, the partial pressures of oxygen at both electrode faces are substantially equivalent. By integrating the pumping current required to transition the internal reference chamber from the empty state to this null or balanced state, the relationship between the total applied charge and the quantity of oxygen transferred can be calculated and stored as a sensor calibration factor.

The pulse based pumping method may be used to cause the sensor internal reference chamber oxygen partial pressure to substantially track a varying, external, unknown gaseous environment oxygen partial pressure by applying current pulses of the appropriate polarity so as to cause the transfer of oxygen into or out of the internal reference chamber such that the two partial pressures remain substantially at null or in balance as indicated by a sensor voltage reading close to zero volts.

By integrating the pumping current required to maintain the null or balanced state an accumulated charge value might be ascertained. This charge value, in conjunction with the aforementioned calibration factor, may be used to calculate the actual oxygen partial pressure inside the internal reference chamber. It follows that this calculated internal partial pressure in conjunction with the measured sensor voltage may be used to calculate an instantaneous oxygen partial pressure value for the external unknown gaseous environment.

With respect to the sensor shown in FIGS. 5 and 6 there is a potential that, due to manufacturability and aggressive external process measurement conditions, leakage paths may negatively affect the ability of the sensor system to cause the sensor internal reference chamber to substantially track and remain quantifiably in balance with the external gaseous environment under investigation. Further, the sensor pumping system described above has the added disadvantage that in situations of very low oxygen partial pressures, whether due to low partial pressures in the external gaseous environment, low partial pressures in a calibration gas, or the reference and external partial pressures being substantially close to a low partial pressure null point, the amount of charge intended to perform a specific pumping action may be greater than the quantity of oxygen available to be pumped thereby causing a potential oscillatory state in the pumping mechanism and/or causing the excess pumping current to disadvantageously polarize the sensor cell. It is therefore desirable to provide an improved pumping method capable of performing a sensor leakage check routine. It is further desired to provide an improved pumping method capable of operation in very low oxygen partial pressure environments.

BRIEF DESCRIPTION OF THE INVENTION

In a first embodiment, the present invention provides for the operation of a solid electrolyte oxygen sensor with a diagnostic leak check function to detect both gross and fine sensor physical leaks. More specifically, the first embodiment controls the application of a steady state current of the proper polarity and specific value so as to cause the sensor internal reference chamber to be emptied of oxygen as determined by the simultaneous measurement of the sensor output voltage. An empirically predetermined time limit value is placed on this emptying process. If the sensor fails to achieve an empty state as defined by a specific, programmed output voltage target value, within the specified time limit, the sensor is considered to have a gross physical leak. If the sensor successfully achieves an empty state, the method controls the stepwise reduction of the application of pumping current to an empirically predetermined low limit value while concurrently attempting to maintain the aforementioned programmed voltage value indicative of an empty sensor. An empirically predetermined time limit value is placed on this pumping current reduction process. If the sensor fails to achieve the predetermined low limit pumping current value within the specified time limit value, the sensor is considered to have a fine physical leak.

In a further aspect of the first embodiment, the initial value of the pumping current pulse magnitude presented to a calibration factor generation process is reduced as a function of the relationship between the oxygen partial pressure of air at a standardized atmospheric pressure and the oxygen partial pressure of a calibration gas against which the sensor is calibrated. The effect of this reduction is to scale down the pumping current in relation to the calibration gas oxygen partial pressure thereby avoiding the potential problem of over pumping the sensor at low oxygen partial pressures.

In a further aspect of the first embodiment, the instantaneous value of the pumping current pulse magnitude presented to a sensor null tracking or zero balancing process is dynamically increased or reduced as a function of the relationship between the oxygen partial pressure of air at a standardized atmospheric pressure and the oxygen partial pressure of the sensor internal reference chamber. The effect of this dynamic manipulation is to further avoid the potential problem of over pumping the sensor at low oxygen partial pressures.

In a further aspect of the first embodiment, the instantaneous values of the pumping current pulse magnitude, pumping current pulse application time and post pumping current pulse relaxation time are dynamically reduced as a function of the instantaneous measured Nernst voltage as the sensor approaches the null or balance point during a calibration or initialization process or during an internal reference tracking process. The effect of this dynamic manipulation is to avoid the potential problem of oscillatory behavior close to the pumped sensor null or balance point.

DETAILED DESCRIPTION OF THE INVENTION

Figure 1:
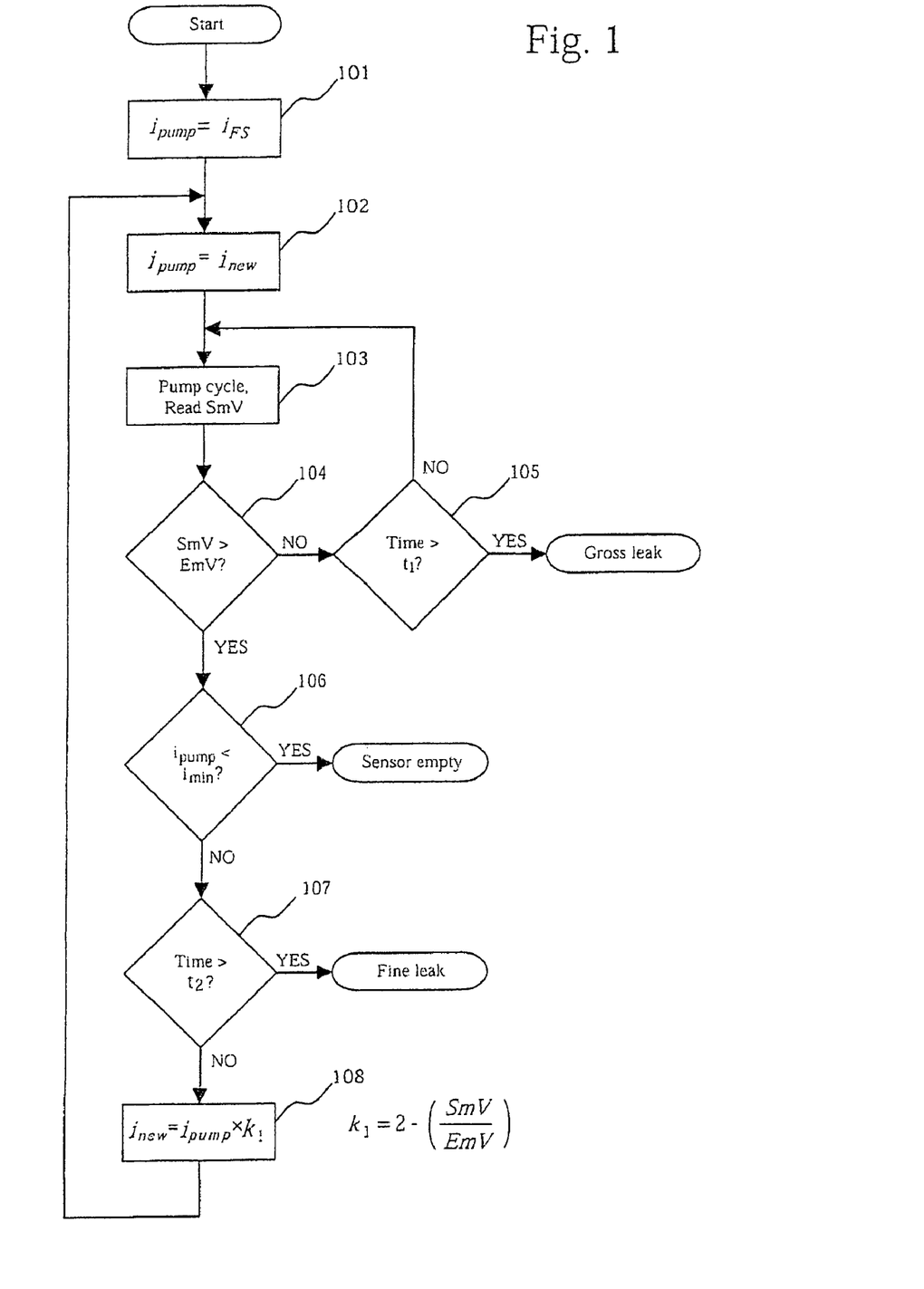
FIG. 1 is a flowchart and related expression showing the routine for performing a simultaneous physical leak check and emptying process on the sealed internal reference chamber of a solid electrolyte oxygen cell.

FIG. 1 shows a method for performing a simultaneous physical leak check and emptying of a sensor sealed reference chamber. In step 101 an intermediate calculation variable $i_{new}$, is set to a first maximum value $i_{FS}$, representing a fixed upper limit to the current available to pump the sensor internal reference chamber. More specifically, this value may represent the maximum design limit of a particular hardware circuit used to effect sensor pumping actions.

In step 102 $i_{pump}$, the pump circuit magnitude control variable is initialized to the starting upper limit value $i_{new}$. The value stored in $i_{pump}$ is passed to the control circuit 20 (FIG. 5) to effect the emptying of the internal reference chamber. Steps 103 through 105 comprise the internal reference chamber pump-out sub-loop, ELoop. Step 103 activates the sensor pumping mechanism within the control circuit 20 and queries the developing sensor output voltage. The DC current value $i_{pump}$ is latched into the control circuit 20 and continuously applied to the electrodes 10, 12 of the sensor in the proper polarity so as to move oxygen ions from the inner electrode surface 12 to the outer electrode surface 10.

The sensor electrodes are also attached to the measurement mechanism of the control circuit 20 whereby the sensor voltage can be queried to determine the instantaneous state of the oxygen partial pressure relationship of the sensor internal reference chamber to the external gaseous environment. The electrodes are attached to the control circuit 20, during any measurement phase, with a polarity such that the emptying of the sensor internal reference chamber will cause the observed voltage to move in a positive direction in the presence of an external oxygen partial pressure environment such as air.

In step 104, a judgment is made as to whether SmV, the instantaneous voltage value of the emptying sensor, is greater than EmV, a preprogrammed value corresponding to the voltage output when the sensor internal reference chamber reaches an empty state. If the judgment is NO, the chamber is not yet empty and control is passed to step 105.

In step 105, the elapsed time since the first occurrence of step 103 within each instance of ELoop is compared against a preprogrammed time value $t_1$. If this elapsed time is greater than $t_1$, the sensor is assumed to have a gross physical leak due to the unintended large backflow of the external gaseous environment into the sensor sealed internal reference chamber. If the elapsed time is less than $t_1$, control is passed back to step 103 and the emptying-measure loop continues.

If the judgment made in step 104 is YES, the sensor is understood to be empty and control is passed to the pumping current reduction phase.

Steps 102 through 108 comprise the pumping current reduction loop, RLoop. In step 106, a judgment is made as to whether the instantaneous value of the pump current magnitude control variable $i_{pump}$ is less than or equal to a preprogrammed lower limit value $i_{min}$. If the judgment is YES, the sensor is considered both empty and leak free and control is passed from method M100 on to the next control phase. If the judgment is NO, control is passed to step 107.

In step 107, the elapsed time since the first RLoop occurrence of step 103 is compared against a preprogrammed time value $t_2$. If this elapsed time is greater than $t_2$, the sensor is assumed to have a fine physical leak due to the unintended low backflow of the external gaseous environment into the sealed internal reference chamber. If the elapsed time is less than $t_2$, control is passed to step 108.

In step 108, the present value of the pumping current applied to the sensor is modified as a function of the relationship of the measured sensor voltage SmV to the preprogrammed empty target voltage EmV by the following expression:

$$i_{new} = i_{pump} \times k_1$$

where:

$$k_1 = 2 - \left(\frac{SmV}{EmV}\right)$$

The intermediate variable, $i_{new}$ holds the output of the calculation in step 108. Control is then passed back to step 102 where the pump circuit magnitude control variable is programmed with the new pumping current set point held in $i_{new}$.

The expression $k_1$ outlined above in step 108 reduces the pumping current $i_{pump}$ in a stepwise fashion with the degree of reduction at each step being a function of the SmV to EmV relationship. Step 104 ensures that an SmV value less than EmV, i.e. sensor NOT empty, will not reach the calculation made in step 108, thereby always effecting a pumping current reduction.

At each execution of RLoop the reduction in step 108 of the pumping current delivered to the sensor electrodes will cause a corresponding reduction in the rate at which the sensor internal reference chamber is further emptied at each ELoop iteration. Time $t_1$ sets the upper limit for the complete loop execution time for any given ELoop instance within RLoop.

Time $t_2$ sets the upper limit for the complete emptying-current reduction process comprised of RLoop and it's nested sub-loop ELoop. In practical terms, time $t_2$ is the upper limit of the cumulative value of all the individual ELoop $t_1$ times as the sensor internal reference chamber attempts to achieve the pumping current limit $i_{min}$.

It is understood that in the presence of a gross physical leak the relatively large gaseous backflow into the sensor internal reference chamber will more than offset the emptying action provided by the pumping current source. In this case, the sensor voltage SmV will never reach the target value EmV within the relatively short time limit of $t_1$. As such, the ELoop action functions as a first order leakage check.

It is further understood that in the presence of a fine physical leak the relatively small gaseous backflow into the sensor internal reference chamber, while NOT impeding the ability of the RLoop reduced pumping current to cause SmV to regain the target EmV within a given ELoop step, will prevent the sensor from reaching the target limiting current $i_{min}$ within the relatively longer time limit of $t_2$. As such, the RLoop action functions as a second order leakage check.

It is anticipated that the steps outlined in method M100 (FIG. 1), comprising a software sequence typically executed from a supervisory program, may be either manually or automatically activated during a sensor calibration or initialization process. Software sequence control will pass from method M100 to method M200 (FIG. 2) to start a sensor calibration process using a calibration gas or to method M300 (FIG. 3), described further on, to start a sensor initialization process on an unknown process environment.

Figure 2:
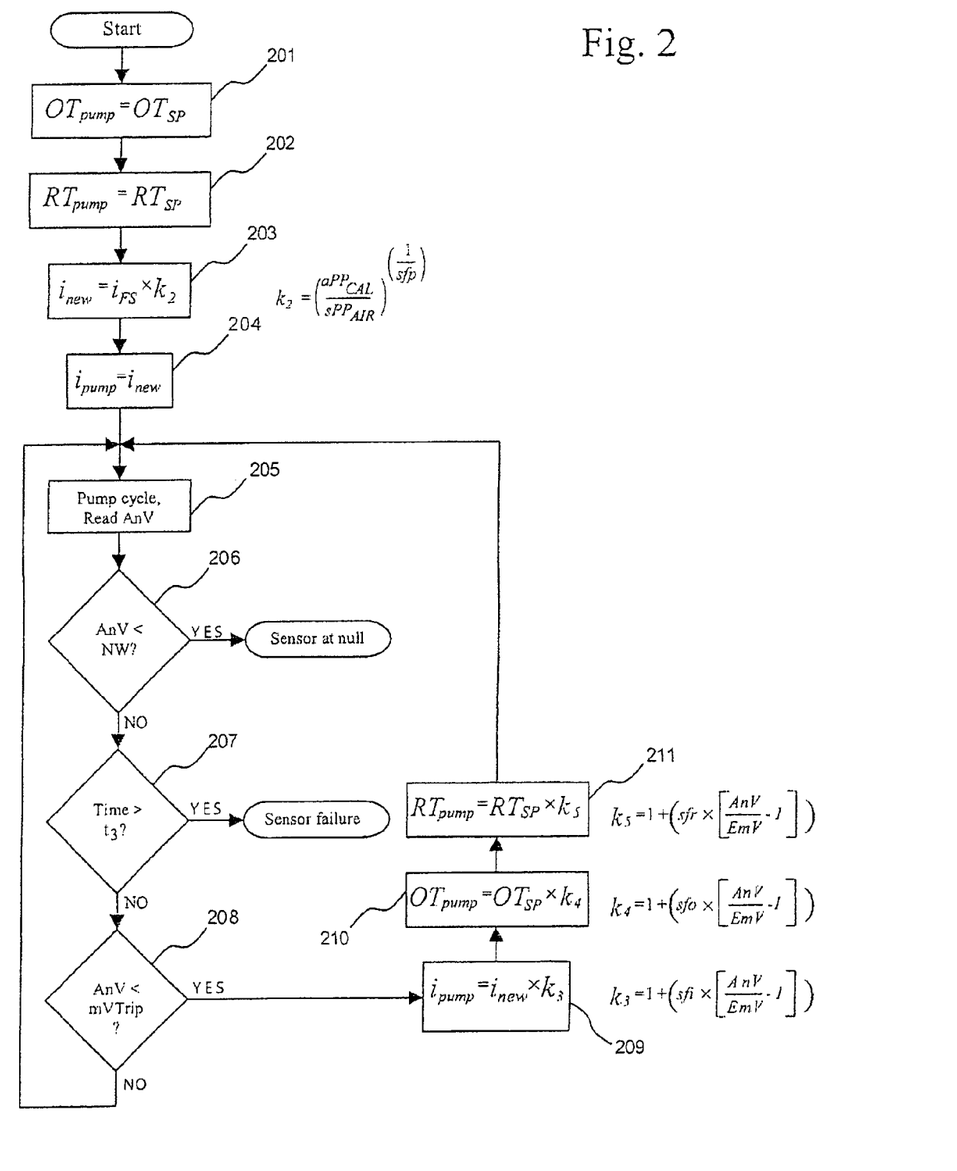
FIG. 2 is a flow chart and related expressions showing the routine for performing a dynamically controlled, null balancing, calibration process on the sealed internal reference chamber of a solid electrolyte oxygen cell.

FIG. 2 shows method M200, whereby the sensor internal reference chamber is nulled or balanced with respect to a known external gaseous environment or calibration gas such as air. Controlled pulses of current are applied to the sensor electrodes in the proper polarity so as to move oxygen ions from the outer electrode surface to the inner electrode surface. The pumping process continues until the measured sensor Nernst voltage is close to zero volts thereby indicating a balance point in which the oxygen partial pressures of the internal reference chamber and the external environment are substantially the same. As is conventionally performed, the applied current pulses are integrated with respect to time and the resultant totalized charge quantity and the now known internal reference oxygen partial pressure value are used to generate a sensor specific calibration factor for further use in process oxygen measurement functions.

In step 201, the pump pulse ON time control variable, $OT_{pump}$ is initialized to a predetermined maximum starting value $OT_{SP}$. $OT_{pump}$ controls the width of the current pulse delivered to the sensor electrodes through the pump control circuit.

In step 202, the pump pulse RELAXATION time control variable, $RT_{pump}$ is initialized to a predetermined maximum starting value $RT_{SP}$. $RT_{pump}$ controls the width of the time interval between the ending of an applied current pulse and the point at which a sensor voltage measurement is made.

In step 203, the intermediate calculation variable $i_{new}$ is initialized to a starting pumping current value where said value is the full-scale current limit $i_{FS}$, conditioned by the relationship of the oxygen partial pressure of the applied calibration gas $aPP_{CAL}$, to the oxygen partial pressure of air, $sPP_{AIR}$ at a standard barometric pressure value. This relationship is defined in the following expression:

$$i_{new} = i_{FS} \times k_2$$

where:

$$k_2 = \left(\frac{aPP_{CAL}}{sPP_{AIR}}\right)^{\left(\frac{1}{sfp}\right)}$$

In an embodiment of the above expression, $sPP_{AIR}$ evaluates to a constant so that the effect of the expression $k_2$ is to reduce the starting pumping current value applied to the sensor electrodes as a function of the external calibration gas oxygen partial pressure $aPP_{CAL}$.

The pump scale factor variable sfp is typically set to a value of 1 causing the reduction effect to be linear with respect to $aPP_{CAL}$ and the amount of time required to effect a calibration null balance to be a constant value independent of $aPP_{CAL}$ and determined purely by the $OT_{SP}$, $RT_{SP}$, and $i_{FS}$ pump factors and the pump reduction expressions and respective scale factors: $k_3$, $k_4$, $k_5$, and sfi, sfo, sfr detailed further on.

Expression $k_2$ matches the required pumping current to the applied calibration gas and eliminates the problem of sensor over pumping at low calibration gas oxygen partial pressures. The pump scale factor variable sfp can be set to a value less than or greater than 1 to accommodate very low oxygen partial pressures or unusual gas dynamics.

In a further embodiment of step 203, a maximum upper limit is placed on the result of the expression $k_2$ such that if the ratio of $aPP_{CAL}$ to $sPP_{AIR}$ evaluates to a value greater than 1, $k_2$ is forced to a value of 1 thereby always limiting the maximum pump current output $i_{pump}$ to $i_{FS}$.

In step 204, $i_{pump}$, the pump circuit magnitude control variable, is initialized to the preconditioned starting upper limit value, $i_{new}$. The value stored in $i_{pump}$ sets the current pulse magnitude value passed to the pump control circuit.

Step 205 activates the pump control mechanism and queries the developing sensor Nernst voltage. A pulse of magnitude $i_{pump}$ and width $OT_{pump}$ is applied to the sensor. At the end of the pulse application a relaxation time of $RT_{pump}$ takes place whereby the pumping current is turned off to allow the sensor output to settle to a stable value. At the end of the relaxation time a voltage measurement is made and the resultant value passed to the next step.

In step 206 a judgment is made as to whether AnV, the absolute value of the measured sensor Nernst voltage, is within the NW or Null Window limit. Null Window is a preprogrammed value corresponding to the required measurement tolerance of the sensor voltage output when the sensor internal reference chamber partial pressure reaches a null or balance point in relation to the external calibration gas partial pressure. Null Window is a limit value controlling the termination of this null balance process. If the judgment is YES that the measured sensor voltage is within the limit specified by Null Window then the sensor is substantially at null or in balance and control is passed from method M200 to the next control phase. If the judgment is NO, the sensor is not yet at the null point and control is passed to step 207.

In step 207 a judgment is made as to whether the elapsed time since the first occurrence of step 205 is greater than a preprogrammed time value $t_3$. If the judgment is YES, the sensor is assumed to have developed a physical and/or electrical failure mode. If the judgment is NO control is passed to step 208.

In step 208 a judgment is made as to whether the value of AnV is less than mVTrip, a preprogrammed value that triggers the activation of the dynamic reduction expressions detailed further on. If the judgment is NO, control is passed back to step 205 and the sensor is again pumped with the pulse parameter values initialized in steps 201 through 204.

If the judgment in step 208 is YES, then control is passed to the dynamic reduction expressions of steps 209, 210 and 211.

In step 209 the pump circuit magnitude control variable value generated in step 203 is further modified as a function of the relationship of AnV to EmV by the following expression:

$$i_{pump} = i_{new} \times k_3$$

where:

$$k_3 = 1 + \left(sfi \times \left[\frac{AnV}{EmV} - 1\right]\right)$$

The scale factor sfi further controls the magnitude of the reduction resulting from this expression.

In step 210 the pump circuit pulse ON time control variable value generated in step 201 is modified as a function of the relationship of AnV to EmV by the following expression:

$$OT_{pump} = OT_{SP} \times k_4$$

where:

$$k_4 = 1 + \left(sfo \times \left[\frac{AnV}{EmV} - 1\right]\right)$$

The scale factor sfo further controls the magnitude of the reduction resulting from this expression.

In step 211 the pump circuit pulse RELAXATION time control variable value generated in step 202 is modified as a function of the relationship of AnV to EmV by the following expression:

$$RT_{pump} = RT_{SP} \times k_5$$

where:

$$k_5 = 1 + \left(sfr \times \left[\frac{AnV}{EmV} - 1\right]\right)$$

The scale factor sfr further controls the magnitude of the reduction resulting from this expression.

The effect of steps 209, 210 and 211 is to apply a breaking or slowing action to the null balance process based on the instantaneous measured Nernst voltage output of the sensor. In a preferred embodiment of the present invention the trigger value mVTrip is programmed to allow for maximum pumping speed, fast null balancing and to keep overall pump system bandwidth as wide as efficiently possible. The new pulse control values generated in the preceding steps are passed back to step 205 for the use during the next pump-measure cycle.

The three reduction expressions $k_3$, $k_4$ and $k_5$ in conjunction with expression $k_2$ match the pumping pulses applied to the sensor electrodes to the instantaneous partial pressure conditions at the electrode surfaces to eliminate the problem of pump oscillations at or near the null balance point.

Upon the successful completion of method M200 it is understood that the oxygen sensor has undergone a calibration process and that a sensor specific calibration factor has been generated and stored for process oxygen measurement use.

Figure 3:
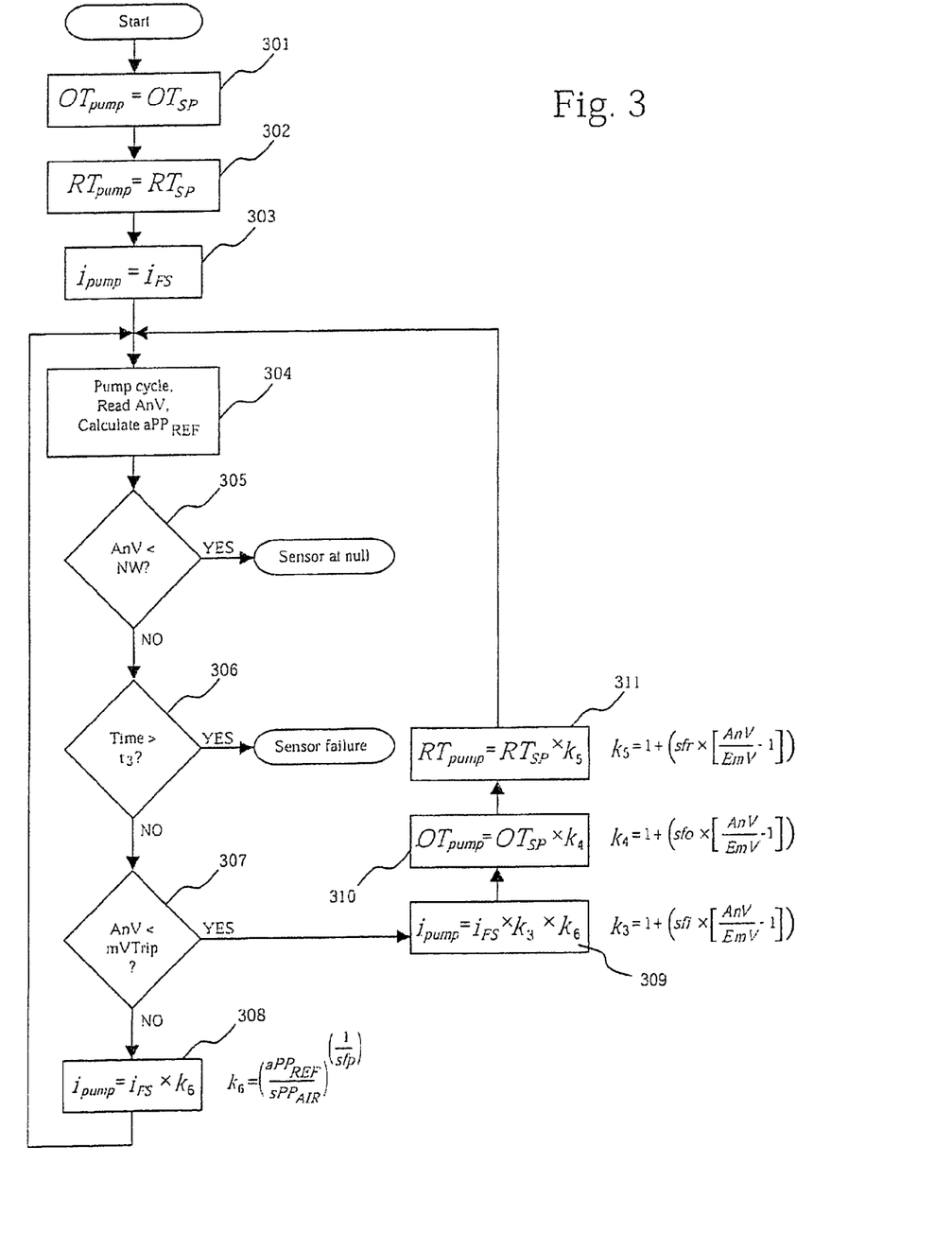
FIG. 3 is a flow chart and related expressions showing the routine for performing a dynamically controlled, null balancing initialization process on the sealed internal reference chamber of a solid electrolyte oxygen cell.

FIG. 3 shows method M300, whereby a sensor internal reference chamber is nulled or balanced with respect to an unknown external gaseous environment. It is observed that method M300 is similar to and shares some steps with method M200. For those steps in M300 that are identical with M200, the reader will be referred to the descriptions of M200 for greater detail.

Method M300 may be manually or automatically activated during a sensor initialization process and would be preceded by method M100 as a first task within this initialization process. Method M300 further anticipates the prior execution of a sensor calibration process comprised of methods M100 and M200.

In steps 301 and 302, the pump circuit control values $OT_{pump}$ and $RT_{pump}$ are initialized as in steps 201 and 202 respectively, of M200.

In step 303 the pump magnitude control variable $i_{pump}$ is initialized to the full-scale pump current limit value $i_{FS}$.

Step 304 activates the pump control mechanism and queries the developing sensor Nernst voltage as in step 205 of M200. Step 304 has the additional function of calculating an initial value of the sensor internal reference chamber oxygen partial pressure, $aPP_{REF}$.

It is anticipated that at the start of method M300 the sensor internal reference chamber is at the empty state due to the action of method M100. The effect of steps 301 through 303 is to define the parameters of the first pumping pulse applied to the sensor electrodes in anticipation of making the first determination of $aPP_{REF}$. This first value of $aPP_{REF}$ is calculated as described in the prior art using the sensor calibration factor and the charge value of the first pumping pulse as determined from $i_{pump}$ and $OT_{pump}$.

In step 305, a judgment is made as to whether the value of AnV is within the preprogrammed NW limit as described in step 206. If the judgment is YES, the sensor is considered to be substantially at null and control is passed from method M300 to the next control phase. If the judgment is NO, the sensor is not yet at the null point and control is passed to step 306.

In step 306, a judgment is made as to whether the elapsed time since the first occurrence of step 304 is greater than the aforementioned time value $t_3$. If the judgment is YES, the sensor is assumed to have developed a physical and/or electrical failure mode. If the judgment is NO, control is passed to step 307.

In step 307, a judgment is made as to whether the value of AnV is less than the mVTrip value as described in step 208. If the judgment is NO, the dynamic reduction trigger point, mVTrip has not been reached and control is passed to step 308. In step 308 the pump magnitude control variable $i_{pump}$ is set to the full-scale pump current limit $i_{FS}$ conditioned by the relationship of the oxygen partial pressure of the sensor internal reference chamber $aPP_{REF}$ calculated in step 304 to the aforementioned constant $sPP_{AIR}$. This relationship is defined in the following expression:

$$i_{pump} = i_{FS} \times k_6$$

where:

$$k_6 = \left(\frac{aPP_{REF}}{sPP_{AIR}}\right)^{\left(\frac{1}{sfp}\right)}$$

As in expression $k_2$, the pump scale factor variable sfp is typically set to a value of 1 causing the manipulation of $k_6$ to be linear in character and as in $k_2$, the result of $k_6$ is forced to a value of 1 in the case where the value of $aPP_{REF}$ is greater than $sPP_{AIR}$.

Expression $k_6$ matches the instantaneous applied pumping current magnitude to the prevailing oxygen partial pressure level in the sensor internal reference chamber so as to avoid the problem of sensor over pumping and resultant disadvantageous electrode polarization at low external process oxygen process partial pressures.

Control is then passed back to step 304 for the next pump cycle using the newly modified value of $i_{pump}$ and the unchanged values of $Ot_{pump}$ and $Rt_{pump}$.

If the judgment in step 307 is YES then control is passed to the dynamic reduction algorithms of steps 309 through 311.

In step 309, the pump current magnitude control variable value is modified as function of two factors; $k_3$ as described in step 209 of method M200 and $k_6$ as described in the previous step 308.

In step 310, the pump circuit pulse ON time control variable value is modified by expression $k_4$ as described in step 210 of method M200.

In step 311, the pump circuit pulse RELAXATION time control variable value is modified by expression $k_5$ as described in step 211 of method M200.

The new pulse control values generated in the above steps are passed back to step 304 for use during the next pump-measure cycle.

As in method M200, the expressions $k_3$, $k_4$ and $k_5$ in steps 309, 310 and 311 apply a breaking or slowing action to the null balance process based on the instantaneous measured Nernst voltage output of the sensor while the addition of expression $k_6$ will either increase or decrease the pumping current magnitude as $aPP_{REF}$ changes.

Upon successful completion of method M300 it is understood that the oxygen sensor has undergone an initialization process on an unknown external process gas. The oxygen partial pressure of the sensor internal reference chamber $aPP_{REF}$, can now be calculated using the totalized charge value required to complete method M300 and the sensor calibration factor generated in method M200. Since the internal and external sensor oxygen partial pressure environments are substantially equal as indicated by the sensor Nernst output being close to zero volts, it follows that the external environment oxygen partial pressure $aPP_{O2}$ should be numerically equal to this calculated $aPP_{REf}$ value.

Figure 4:
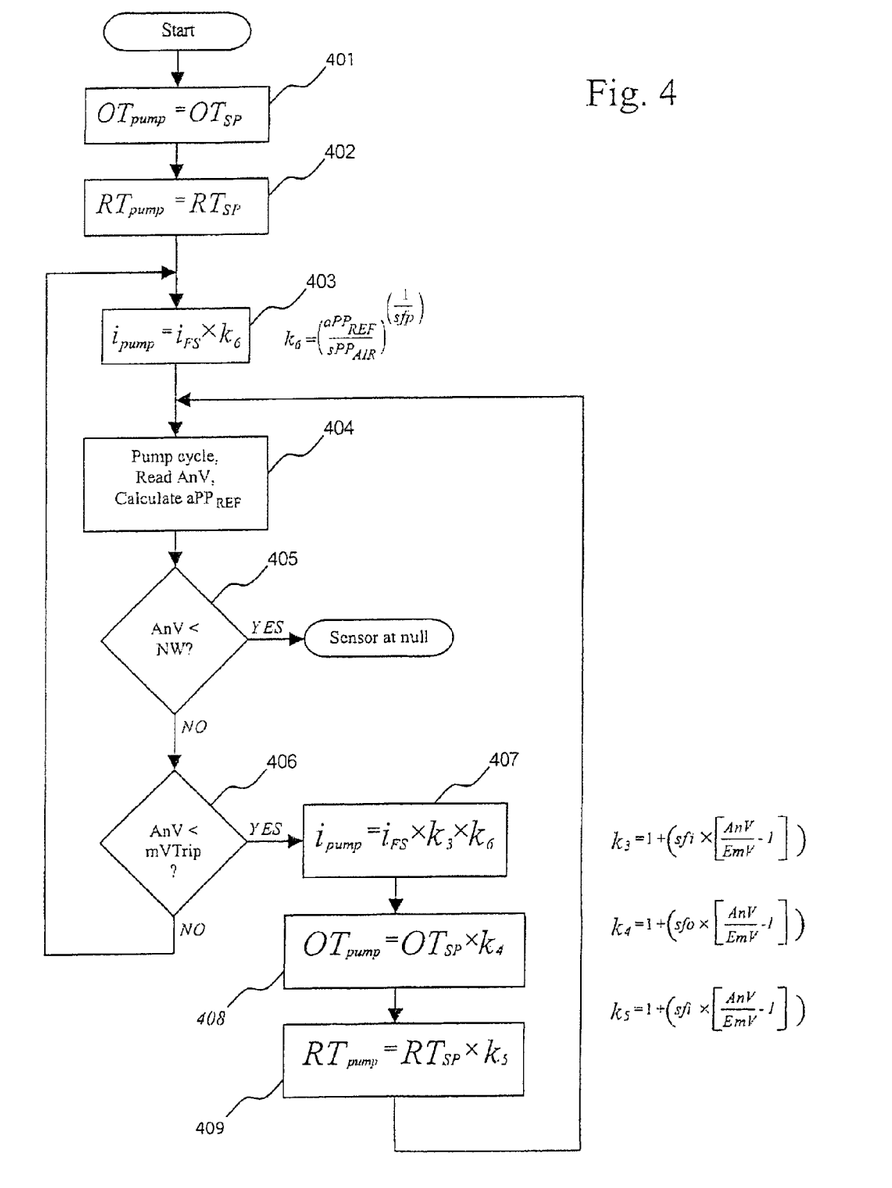
FIG. 4 is a flow chart and related expressions showing the routine for performing a dynamically controlled, re-null tracking process on the sealed internal reference chamber of a solid electrolyte oxygen cell.

FIG. 4 shows a method M400, whereby a sensor sealed internal reference chamber may be renulled or rebalanced with respect to a changing unknown external gaseous environment. It is observed that method M400 is similar to and shares some steps with methods M200 and M300. The reader will be referred to the appropriate steps of the preceding methods for greater descriptive detail where steps share identical functions.

Method M400 may be automatically activated from a supervisory program during a measuring process when a predetermined condition is met. Method M400 further anticipates the prior execution of a sensor calibration process comprised of methods M100 and M200 and a sensor initialization process comprised of methods M100 and M300. Method M400 may be activated from an external process environment measurement mode when the sensor Nernst voltage output crosses a predetermined threshold, RenullTrip. RenullTrip defines the maximum ratiometric internal to external oxygen partial pressure imbalance allowable before a null tracking operation is activated.

In steps 401 and 402, the pump circuit control variables $OT_{pump}$ and $RT_{pump}$ are initialized as in steps 201 and 202 respectively, of M200. In step 403 the pump magnitude control variable $i_{pump}$ is set to the full scale pump current limit $i_{FS}$ conditioned by the relationship of $aPP_{REF}$ to $sPP_{AIR}$ as described in step 308 of method M300. At the start of method M400, the present value of $aPP_{REF}$ is known and in use by a supervisory program in the calculation of prevailing external process environment oxygen partial pressure values. As such, this known $aPP_{REF}$ value is used with expression $k_6$ as described in step 308 to effect a pumping current modification based on the sensor internal reference chamber oxygen partial pressure.

Step 404 activates the pump control mechanism, queries the developing sensor Nernst voltage and updates the value of $aPP_{REF}$ based on the applied charge preset in steps 401 and 403 and the aforementioned sensor calibration factor. In step 405 a judgment is made as to whether the value of AnV is within the NW limit as described in step 206. If the judgment is YES, the sensor is considered to be substantially at null and control is passed from method M400 back to the supervisory program. If the judgment is NO, the sensor is not yet at the null point and control is passed to step 406.

In step 406, a judgment is made as to whether the value of AnV is less than the mVTrip value as described in step 208. If the judgment is NO, the dynamic reduction trigger point, mVTrip has not been reached and control is passed back to step 403 using the updated value of aPP$_{REF}$. If the judgment in step 406 is YES then control is passed to the dynamic reduction algorithms of steps 407 through 409. In step 407 the pump current magnitude control variable value is modified as function of two factors; k$_3$ as described in step 209 of method M200 and k$_6$ as described in the step 308 of method M300. In step 408 the pump circuit pulse ON time control variable value is modified by expression k$_4$ as described in step 210 of method M200. In step 409 the pump circuit pulse RELAXATION time control variable value is modified by expression k$_5$ as described in step 211 of method M200. The new pulse control values generated in the above steps are passed back to step 404 for use during the next pump-measure cycle.

As in method M200, the expressions k$_3$, k$_4$ and k$_5$ in steps 407, 408 and 409 apply a breaking or slowing action to this renull tracking process based on the instantaneous measured Nernst voltage output of the sensor while the addition of expression k$_6$ will either increase or decrease the pumping current magnitude as aPP$_{REF}$ changes. Expression k$_6$ matches the instantaneous applied pumping current magnitude to the prevailing oxygen partial pressure level in the sensor internal reference chamber so as to avoid the problem of sensor over pumping and resultant disadvantageous electrode polarization at low external process oxygen process partial pressures. As described, the actions of method M400 are controlled by three settings. The RenullTrip value determines the starting point of the method. The mvtrip value determines the activation point of the dynamic reduction expressions. The Null Window value determines the null point or stopping point of this renull tracking process. Upon successful completion of method M400 it is understood that the internal and external sensor environments have again achieved a null or balanced point and control is passed back to a supervisory program to resume process measurement activities.

The invention contemplates other embodiments wherein the sensor system is multi-celled in construction and the present methods and expressions control a pump cell separately from a measurement cell. The invention further contemplates the use of a single set or multiple sets of the aforementioned pump tuning variables for the methods and expressions described.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for pumping a sealed internal reference chamber of a solid electrolyte oxygen sensor, having an internal electrode and an external electrode, during a dynamically controlled, null balancing, calibration process, said method comprising:
   a. initializing a set of pumping current pulse parameters controlling pulse ON time, post pulse RELAXATION time and pulse magnitude;
   b. applying a pulsed pumping current based on said set of pulse parameters to the internal and external electrodes, wherein the application of current transitions the chamber from a substantially evacuated state to a substantially null or balanced oxygen partial pressure state with respect to an applied external calibration gaseous environment;
   c. periodically comparing the Nernst voltage of the sensor to a predetermined limit to determine whether the chamber is at a null or balanced state;
   d. comparing an elapsed time from the application of said pulsed pumping current to a third predetermined time limit to determine if the sensor has failed, and
   e. progressively reducing at least one of the magnitude, ON time and RELAXATION time of said pumping current pulses to slow the transition as the chamber approaches the null or balanced oxygen partial pressure state.

2. The method of claim 1 further comprising initializing a pump current pulse ON time control variable OT$_{pump}$ to a first maximum preprogrammed value OT$_{SP}$.

3. The method of claim 1 further comprising initializing a pump current pulse RELAXATION time control variable RT$_{pump}$ to a first maximum preprogrammed value RT$_{SP}$.

4. The method of claim 1 further comprising initializing a pump magnitude control variable i$_{pump}$ via an intermediate calculation variable i$_{new}$ to a first maximum value i$_{FS}$ according to:

$$i_{new} = i_{FS} \times k_2$$

where:

$$k_2 = \left(\frac{aPP_{CAL}}{sPP_{AIR}}\right)^{\left(\frac{1}{sfp}\right)}$$

where aPP$_{CAL}$ represents an oxygen partial pressure of a calibration gas applied to an external environment of the sensor, sPP$_{AIR}$ represents an oxygen partial pressure of air at a standard barometric pressure value, and where an output result of expression k$_2$ is maximally limited to a value of 1 in a case where the value of aPP$_{CAL}$ is greater than a value of sPP$_{AIR}$.

5. The method of claim 1, wherein the method further comprises a sensor nulling loop comprising:
   measuring the Nernst voltage across the electrodes;
   based on said voltage, determining whether the sensor is at the null state;
   if the sensor is not at the null state, determining whether an elapsed time during the nulling loop exceeds a third preprogrammed time limit, and
   if the elapsed time does not exceed the time limit, dynamically reducing the pumping current pulse parameters and repeating the nulling loop.

6. The method of claim 1 wherein the looped steps of the method repeat until AnV is less than the Null Window or the elapsed time value exceeds t$_3$.

7. A method for pumping a sealed internal reference chamber of a solid electrolyte oxygen sensor, having an internal electrode and an external electrode, during a dynamically controlled, null balancing, initialization process, said method comprising:
   a. initializing a set of pumping current pulse parameters controlling pulse ON time, post pulse RELAXATION time and pulse magnitude;
   b. applying a pulsed pumping current based on said set of pulse parameters to the internal and external electrodes, wherein the application of current transitions the chamber from a substantially evacuated state to a substantially null or balanced oxygen partial pressure state with respect to an applied external unknown gaseous environment;

c. periodically comparing the Nernst voltage of the sensor to a predetermined limit to determine whether the chamber is at a null or balanced state;

d. comparing an elapsed time from the application of said pulsed pumping current to a third predetermined time limit to determine if the sensor has failed, and e. progressively reducing at least one of the magnitude, ON time and RELAXATION time of said pumping current pulses to slow the transition as the chamber approaches the null or balanced oxygen partial pressure state.

8. The method of claim 7 further comprising initializing a pump current pulse ON time control variable $OT_{pump}$ to a first maximum preprogrammed value $OT_{SP}$.

9. The method of claim 7 further comprising initializing a pump current pulse RELAXATION time control variable $RT_{pump}$ to a first maximum preprogrammed value $RT_{SP}$.

10. The method of claim 7 further comprising initializing a pump magnitude control variable $i_{pump}$ to a first maximum value $i_{FS}$.

11. The method of claim 7 wherein the method further comprises a sensor nulling loop comprising:
measuring the Nernst voltage across the electrodes;
based on said voltage, determining whether the sensor is at the null state;
if the sensor is not at the null state, determining whether an elapsed time during the nulling loop exceeds a third preprogrammed time limit, and
if the elapsed time does not exceed the time limit, dynamically reducing the pumping current pulse parameters and repeating the nulling loop, and
modifying a pumping current applied to the sensor electrodes.

12. The method of claim 11 wherein the measurement of the condition of the sensor in a first iteration of said nulling loop applies a pump pulse and relaxation interval to said sensor to establish a first oxygen partial pressure $aPP_{REF}$ in the chamber.

13. The method of claim 11 wherein the sensor null state determination further comprises comparing a sensor absolute Nernst voltage value AnV to a preprogrammed target value Null Window such that a value of AnV less than the Null Window value indicates the sensor is at the null or balanced state.

14. The method of claim 11, wherein the elapsed time limit determination further comprises:
comparing the measured elapsed time from a first application of the pumping current in a first iteration of said nulling loop to the preprogrammed time limit value $t_3$, and
determining the sensor to have failed if the elapsed time is greater than $t_3$.

15. The method of claim 11 further comprising a dynamic reduction process that comprises:
comparing a sensor Nernst voltage absolute value AnV to a preprogrammed trip value mVTrip, such that an AnV value less than mVTrip triggers a set of pump pulse dynamic reduction expressions in an alternate sensor nulling loop and
an AnV value greater than mVTrip triggers repetition of the sensor nulling loop using the first initialized pump pulse ON time and RELAXATION time parameters.

16. The method of claim 11 further comprising a sensor pumping current magnitude modification step, which adjusts a currently applied pumping current value $i_{pump}$ in accordance with:

$$i_{pump} = i_{FS} \times k_6$$

where:

$$k_6 = \left(\frac{aPP_{REF}}{sPP_{AIR}}\right)^{\left(\frac{1}{sfp}\right)}$$

where $aPP_{REF}$ represents an oxygen partial pressure of the sensor sealed internal reference chamber, $sPP_{AIR}$ represents an oxygen partial pressure of air at a standard barometric pressure value, and where an output result of the expression $k_6$ is maximally limited to a value of 1 in a case where $aPP_{REF}$ is greater than $sPP_{AIR}$.

17. The method of claim 7 wherein the looped steps of the method repeat until AnV is less than the Null Window or the elapsed time value exceeds $t_3$.

18. A method for pumping a sealed internal reference chamber of a solid electrolyte oxygen sensor, having an internal electrode and an external electrode, during a dynamically controlled, renull tracking or rebalancing process, said method comprising:

a. initializing a set of pumping current pulse parameters controlling pulse ON time, post pulse relaxation time and pulse magnitude;

b. applying a pulsed pumping current based on said set of pulse parameters to the internal and external electrodes, wherein the application of current transitions the chamber from an unbalanced state to a substantially null or balanced state with respect to an applied external unknown gaseous environment;

c. periodically comparing the Nernst voltage of the sensor to a predetermined limit to determine whether the chamber is at the null or balanced state, and d. progressively reducing at least one of the magnitude, ON time and relaxation time of said pumping current pulses to slow the transition as the chamber approaches the null or balanced oxygen partial pressure state.

19. The method of claim 18 further comprising initializing a pump current pulse ON time control variable $OT_{pump}$ to a first maximum preprogrammed value $OT_{SP}$.

20. The method of claim 18 further comprising initializing a pump current pulse relaxation time control variable $RT_{pump}$ to a first maximum preprogrammed value $RT_{SP}$.

21. The method of claim 18 wherein the method further comprises a sensor nulling loop comprising:
modifying a pumping current applied to the sensor electrodes;
measuring the Nernst voltage across the electrodes;
based on said voltage, determining whether the sensor is at the null state;
if the sensor is not at the null state, dynamically reducing the pumping current pulse parameters and repeating the nulling loop.

22. The method of claim 18 wherein the looped steps of the method repeat until AnV is less than the Null Window.

* * * * *